United States Patent
Chen et al.

(10) Patent No.: US 10,584,139 B2
(45) Date of Patent: Mar. 10, 2020

(54) MULTI-BRANCHED CATIONIC PHOSPHONIUM SALT, FORWARD OSMOSIS EXTRACT EMPLOYING THE SAME AND FORWARD OSMOSIS SEAWATER DESALINATION PROCESS

(71) Applicant: INDUSTRIAL TECHNOLOGY RESEARCH INSTITUTE, Chutung, Hsinchu (TW)

(72) Inventors: Yi-Chun Chen, Hsinchu (TW); Meei-Yu Hsu, Hsinchu (TW); Ya-Huei Ho, Jinsha Township (TW); Kai-Chi Chen, Tsautuen Jen (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/994,193

(22) Filed: May 31, 2018

(65) Prior Publication Data
US 2018/0346496 A1  Dec. 6, 2018

(30) Foreign Application Priority Data
Jun. 1, 2017 (TW) .............................. 106118071 A
May 17, 2018 (TW) .............................. 107116774 A

(51) Int. Cl.
| | | |
|---|---|---|
| C07C 309/30 | (2006.01) | |
| C07C 53/15 | (2006.01) | |
| C07F 9/54 | (2006.01) | |
| B01D 61/00 | (2006.01) | |
| C02F 1/44 | (2006.01) | |
| C07C 63/08 | (2006.01) | |
| C07C 65/10 | (2006.01) | |
| C07C 53/18 | (2006.01) | |
| C02F 103/08 | (2006.01) | |

(52) U.S. Cl.
CPC .......... *C07F 9/5449* (2013.01); *B01D 61/005* (2013.01); *C02F 1/445* (2013.01); *C07C 53/15* (2013.01); *C07C 53/18* (2013.01); *C07C 63/08* (2013.01); *C07C 65/10* (2013.01); *C07C 309/30* (2013.01); *C07F 9/5407* (2013.01); *C02F 2103/08* (2013.01); *C02F 2305/00* (2013.01)

(58) Field of Classification Search
CPC .................................................... C07C 53/15
See application file for complete search history.

(56) References Cited

U.S. PATENT DOCUMENTS

| | | |
|---|---|---|
| 4,154,948 A | 5/1979 | Redmore |
| 9,352,286 B2 | 5/2016 | Na et al. |
| 9,447,239 B2 | 9/2016 | Jung et al. |
| 9,492,789 B2 | 11/2016 | Kim et al. |
| 2012/0211423 A1 | 8/2012 | Kim et al. |

(Continued)

FOREIGN PATENT DOCUMENTS

| | | |
|---|---|---|
| CN | 202440382 U | 9/2012 |
| CN | 104994938 A | 10/2015 |

(Continued)

OTHER PUBLICATIONS

Kim et al., "Thermo-responsive Oligomeric poly(tetrabutylphosphonium styrenesulfonate)s as Draw Solutes for Forward Osmosis (FO) Applications," Desalination, vol. 381, 2016 (Available online Dec. 17, 2015), pp. 84-94.

(Continued)

*Primary Examiner* — Ana Z Muresan
(74) *Attorney, Agent, or Firm* — Birch, Stewart, Kolasch & Birch, LLP

(57) ABSTRACT

A multi-branched cationic phosphonium salt is provided. The multi-branched cationic phosphonium salt has a structure represented by formula (I):

$$\{Z[P^+(R^1)(R^2)(R^3)]_n\}(X^-)_n \qquad (I)$$

wherein each of $R^1$, $R^2$, and $R^3$ is independently a linear or branched $C_1$~$C_{10}$ alkyl group, $X^-$ is an organic or inorganic anion, and Z has a structure represented by Formula (IIb) or Formula (IIc):

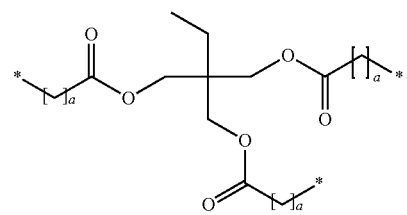

Formula (IIb)

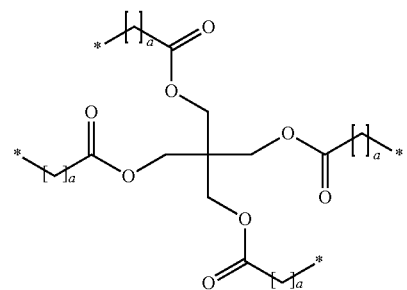

Formula (IIc)

wherein a is an integer of 1~15. In Formulas (IIb) and (IIc), Z is connected to $[P^+(R^1)(R^2)(R^3)]$ at the position marked by an asterisk (*), and n is an integer of 3~4.

13 Claims, 4 Drawing Sheets

(56) References Cited

U.S. PATENT DOCUMENTS

| | | |
|---|---|---|
| 2013/0180919 A1 | 7/2013 | Kim et al. |
| 2013/0240444 A1 | 9/2013 | Jung et al. |
| 2013/0306551 A1 | 11/2013 | Weber et al. |
| 2014/0158622 A1 | 6/2014 | Yanase et al. |
| 2014/0217014 A1 | 8/2014 | Na et al. |
| 2016/0082391 A1 | 3/2016 | Hu et al. |

FOREIGN PATENT DOCUMENTS

| | | |
|---|---|---|
| CN | 105597540 A | 5/2016 |
| JP | 2008-507556 A | 3/2008 |
| WO | WO 2014/175833 A1 | 10/2014 |
| WO | WO 2015/147749 A1 | 10/2015 |
| WO | WO 2016/027865 A1 | 2/2016 |

OTHER PUBLICATIONS

Kohno et al., "Ionic Liquid-derived Charged Polymers to Show Highly Thermoresponsive LCST-type Transition with Water at Desired Temperatures," Chem. Commun., vol. 48, 2012 (Published Oct. 23, 2012), pp. 11883-11885.

Kohno et al., "Thermoresponsive Polyelectrolytes Derived from Ionic Liquids," Polym. Chem., vol. 6, 2015 (Published on Jan. 7, 2015), pp. 2163-2178.

Men et al., "Cationic Poly(ionic liquid) with Tunable Lower Critical Solution Temperature-Type Phase Transition," ACS Macro Letters, vol. 2, 2013 (Published May 9, 2013), pp. 456-459.

Noh et al., "Novel Lower Critical Solution Temperature Phase Transition Materials Effectively Control Osmosis by Mild Temperature Changes," Chem. Commun., vol. 48, 2012 (Published Feb. 24, 2012), pp. 3845-3847.

Ohki et al., "Dionium Cations as Novel Sensing and Separation Reagents for Phthalates in Ion-Selective Electrode Method and in Ion-Pair Chromatography," Analytical Sciences, vol. 6, No. 4, Aug. 1990, pp. 585-588.

Taiwanese Office Action and Search Report, dated Oct. 11, 2017, for Taiwanese Application No. 106118071.

Taiwanese Notice of Allowance for Appl. No. 107116774 dated Feb. 27, 2019.

Japanese Office Action and English translation dated Jun. 4, 2019, for Japanese Application No. 2018-106103.

MULTI-BRANCHED CATIONIC PHOSPHONIUM SALT, FORWARD OSMOSIS EXTRACT EMPLOYING THE SAME AND FORWARD OSMOSIS SEAWATER DESALINATION PROCESS

CROSS REFERENCE TO RELATED APPLICATIONS

The present application is based on, and claims priority from, Taiwan Application Serial Number 106118071, filed on Jun. 1, 2017, and Taiwan Application Serial Number 107116774, filed on May 17, 2018, which is a Continuation-In-Part of Taiwan Application Serial Number 106118071, the disclosure of which are hereby incorporated by reference herein in its entirety.

TECHNICAL FIELD

The disclosure relates to a multi-branched cationic phosphonium salt, a forward osmosis extract employing the same and a forward osmosis seawater desalination process.

BACKGROUND

With the increase in population, rapid industrial development and environmental changes, the world is facing a serious shortage of freshwater resources. More and more countries have begun to develop seawater desalination technology to cope with this global crisis. The technologies commonly used in seawater desalination at present include multi-stage flash distillation (MSF), low-temperature multi-effect distillation (MED), and reverse osmosis (RO). However, these technologies commonly have defects including high cost, high energy consumption, and low water production.

In recent years, forward osmosis (FO) seawater desalination technology has been widely examined. According to the principle of forward osmosis, the forward osmosis seawater desalination technology uses draw solutions (DS) with a high osmotic pressure to separate seawater and get fresh water. Although the forward osmosis seawater desalination technology has advantages over other technologies, such as its lower cost, lower energy consumption, and higher water production, appropriate draw solutions are still required to truly achieve a low-cost water production process.

Generally, polymer material has problems with solubility and high viscosity, so it is difficult to formulate a high-concentration solution using a polymer material. Thus, the osmotic pressure of the solution cannot be further increased. Although the low molecular weight polymer material has better solubility and can be formulated to form a high-concentration solution, the osmotic pressure is still not enough.

Many draw solutions may have a sufficiently high osmotic pressure; however, it is not suitable for practical promotion due to the high energy consumption. For example, while increasing the solubility or osmotic pressure of the draw solution by introducing carbon dioxide, additional processes of heating to 60° C. or higher are needed to remove carbon dioxide when recycling the draw solution. Therefore, higher energy consumption is needed. In addition, magnetic nanoparticles are reported to have been used as a draw solution and recycled by magnetic separation to realize the recirculation of the draw solution. However, in fact, the agglomerated magnetic particles are not easily dispersed again. Moreover, it is also difficult to remove the magnetic nanoparticles.

Therefore, a novel draw solution (extract) material is needed.

SUMMARY

An embodiment of the disclosure provides a multi-branched cationic phosphonium salt, having a structure represented by Formula (I):

$$\{Z[P^+(R^1)(R^2)(R^3)]_n\}(X^-)_n \qquad (I)$$

In formula (I), each of $R^1$, $R^2$, and $R^3$ is independently linear or branched $C_1$~$C_{10}$ alkyl group, $X^-$ is an organic or inorganic anion, and Z has a structure represented by Formula (IIb) or Formula (IIc):

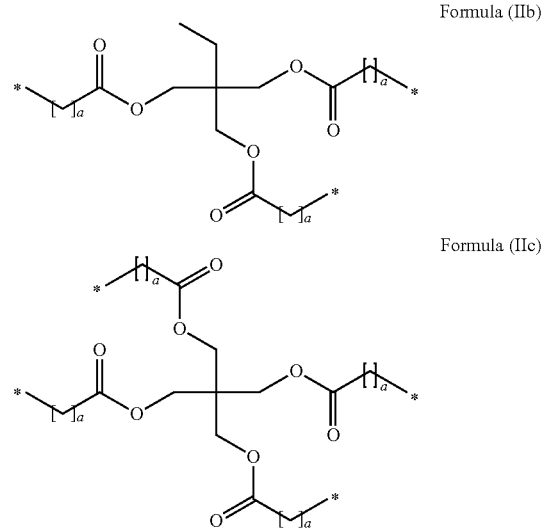

wherein a is an integer of 1~15. In Formulas (IIb) and (IIc), Z is connected to $[P^+(R^1)(R^2)(R^3)]$ at the position marked by an asterisk (*), wherein n is an integer of 3~4.

Another embodiment of the disclosure provides a multi-branched cationic phosphonium salt, having a structure represented by Formula (III):

$$\{Z[P^+(R)_3]_n\}(X^-)_n \qquad (III)$$

In formula (III), R is linear or branched $C_1$~$C_{10}$ alkyl group, $X^-$ is an organic or inorganic anion, and Z has a structure represented by Formula (IIb) or Formula (IIc):

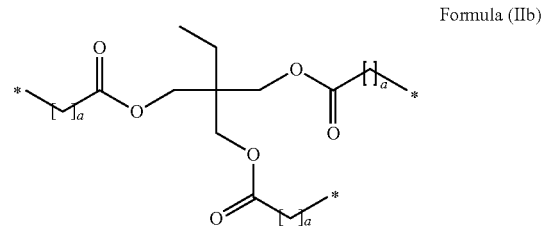

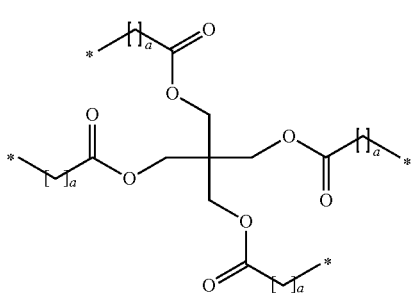

Formula (IIc)

wherein a is an integer of 1~15. In Formulas (IIb) and (IIc), Z is connected to [P⁺(R)₃] at the position marked by an asterisk (*), wherein n is an integer of 3~4.

Another embodiment of the disclosure provides a forward osmosis extract, including a multi-branched cationic phosphonium salt and water. The multi-branched cationic phosphonium salt has a structure represented by Formula (I):

$$\{Z[P^+(R^1)(R^2)(R^3)]_n\}(X^-)_n \quad (I)$$

wherein each of $R^1$, $R^2$, and $R^3$ is independently linear or branched $C_1$~$C_{10}$ alkyl group, $X^-$ is an organic or inorganic anion, Z has a structure represented by Formula (IIa), Formula (IIb), Formula (IIc) or Formula (IId):

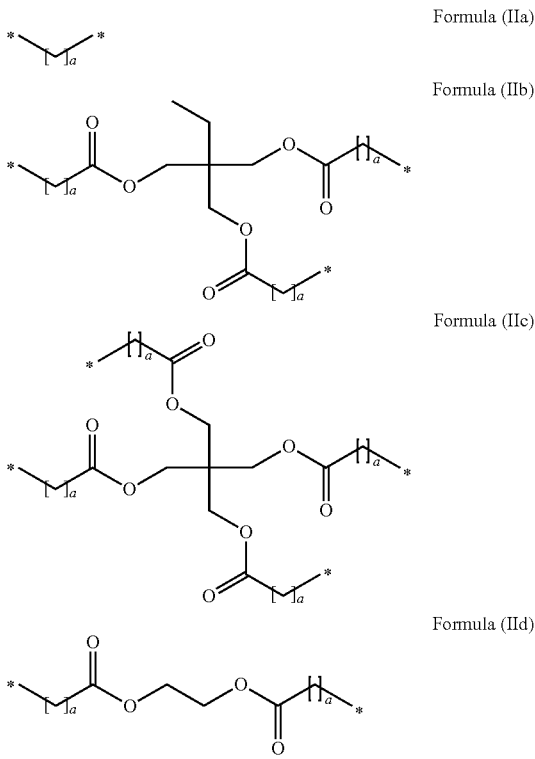

Formula (IIa)

Formula (IIb)

Formula (IIc)

Formula (IId)

wherein a is an integer of 1~15, in Formulas (IIa)~(IId), Z is connected to [P⁺(R¹)(R²)(R³)] at the position marked by an asterisk (*), wherein n is an integer of 2~4. The concentration of the forward osmosis extract is greater than or equal to 5 wt %.

Another embodiment of the disclosure provides a forward osmosis seawater desalination process, including: providing the aforementioned forward osmosis extract and pure water on two sides of a semi-permeable membrane, respectively; and desalinating seawater by using a forward osmosis (FO) model.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1:
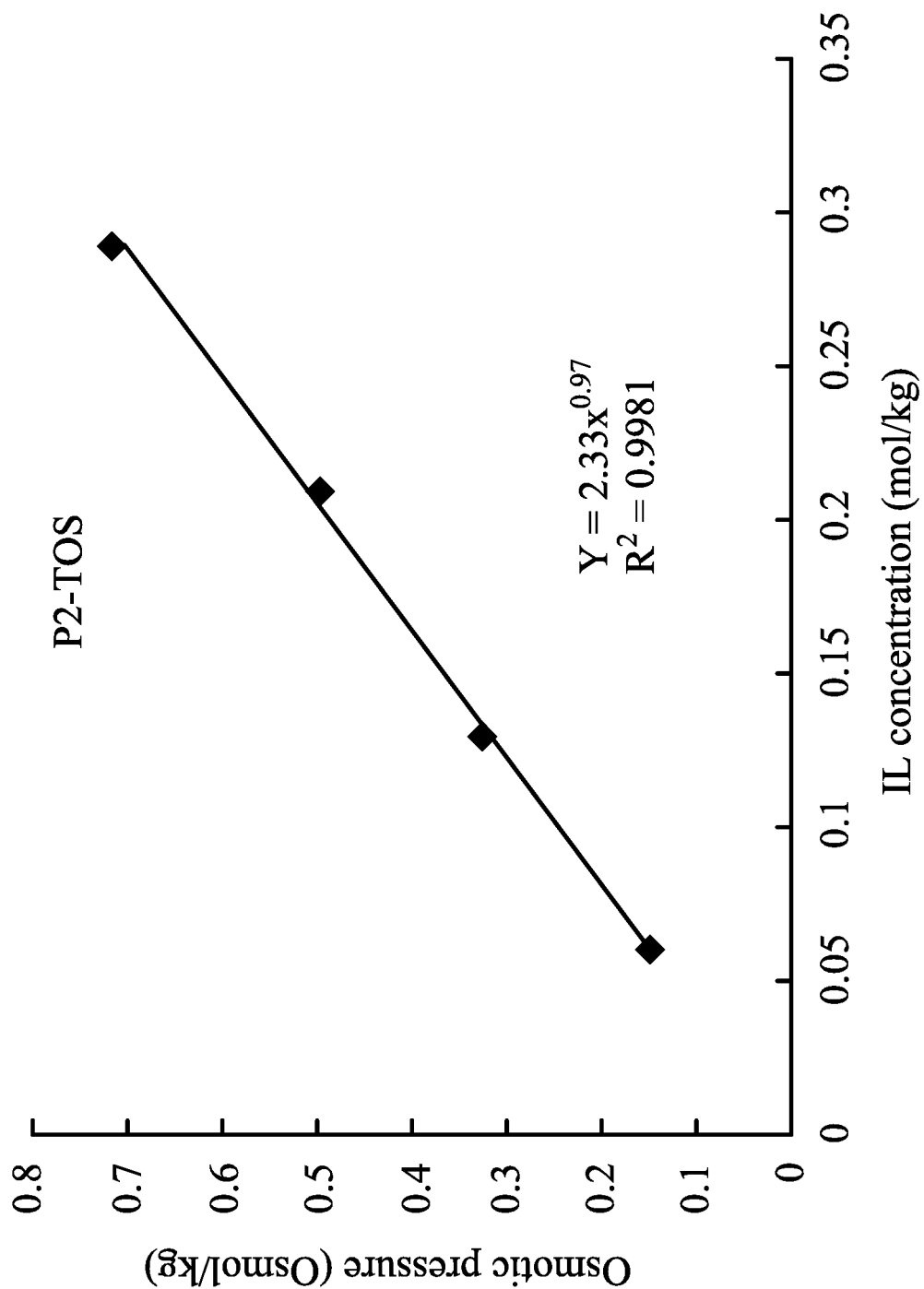
FIG. 1 illustrates the data graph of the actually obtained osmotic pressure and ionic liquid (IL) concentration of P2-TOS.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

According to embodiments of the present disclosure, the present disclosure provides a multi-branched cationic phosphonium salt, which can be used as an extract during the forward osmosis process. For example, the multi-branched cationic phosphonium salt can be used as a forward osmosis extract during the seawater desalination process. However, the application of the multi-branched cationic phosphonium salt provided by the present disclosure is not limited thereto. As long as the concentration and osmotic pressure of the formulated extract is adjusted, the multi-branched cationic phosphonium salt can be used as an extract in other separation processes following the principle of forward osmosis. For example, it can also be applied to wastewater treatment, concentration and purification, extraction, water desalination, power generation, and so on.

The present disclosure uses chemical synthesis method to modify the cation portion of tetrabutylphosphonium p-toluenesulfonate [P₄₄₄₄][TOS] to synthesize a multi-branched cationic oligomers, such as multi-branched cationic dimers (P2) or multi-branched cationic trimers (P3).

In one embodiment of the present disclosure, a multi-branched cationic phosphonium salt having a structure represented by Formula (I) is provided.

$$\{Z[P^+(R^1)(R^2)(R^3)]_n\}(X^-)_n \quad (I)$$

In some embodiments of the present disclosure, each of $R^1$, $R^2$, and $R^3$ may be independently linear or branched $C_1$~$C_{10}$ alkyl group, and Z may have a structure represented by Formula (IIb) or Formula (IIc):

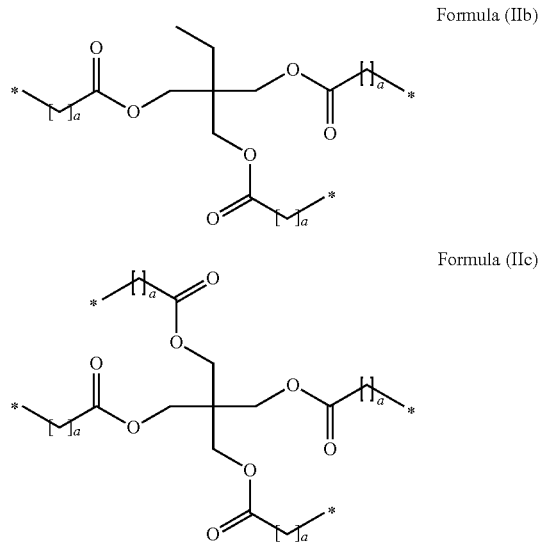

Formula (IIb)

Formula (IIc)

wherein a is an integer of 1~15. In Formulas (IIb) and (IIc), Z is connected to [P$^+$(R$^1$)(R$^2$)(R$^3$)] at the position marked by an asterisk (*), wherein n is an integer of 3~4.

In some embodiments of the present disclosure, X$^-$ in Formula (I) may be an organic or inorganic anion with monovalent. For example, X$^-$ may be $CH_3SO_3^-$, I$^-$, $CF_3COO^-$, $SCN^-$, $BF_4^-$, $CF_3SO_3^-$, $PF_6^-$, $FeCl_4^-$,

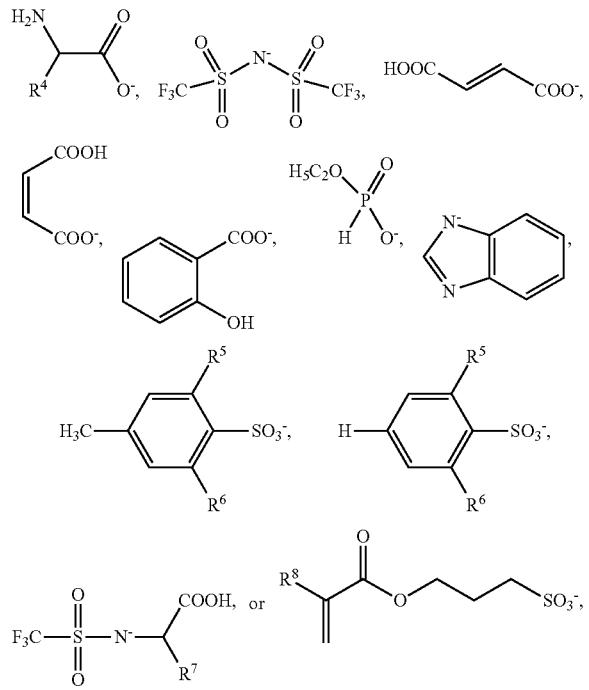

wherein $R^4$ may be —$CH_2COOH$ or —$(CH_2)_4$—$NH_2$; $R^5$ and $R^6$ may be H or $CH_3$; $R^7$ may be —$CH(CH_3)_2$, —$(CH_2)_2$—$CH(CH_3)_2$, —$CH(CH_3)$—$CH_2$—$CH_3$, or —$CH_2$—$C_6H_5$; $R^8$ may be $CH_3$ or H.

In Formula (I), the synthesized multi-branched cationic phosphonium salt may have different characteristics when the central structure Z is collocated with different anions. Appropriate anions may be selected according to demand.

In one embodiment of the present disclosure, X$^-$ in Formula (I) may be

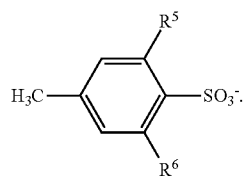

In the embodiment where both $R^5$ and $R^6$ are H, X$^-$ is p-toluenesulfonyl (TOS). In the embodiment where both $R^5$ and $R^6$ are $CH_3$, X$^-$ is trimethylbenzenesulfonate (TMBS).

In one embodiment of the present disclosure, each of $R^1$, $R^2$, and $R^3$ in Formula (I) is independently $C_1$~$C_8$ alkyl groups. In another embodiment of the present disclosure, each of $R^1$, $R^2$, and $R^3$ in Formula (I) is independently $C_1$~$C_5$ alkyl groups.

In one embodiment of the present disclosure, a in Formulas (IIb) and (IIc) may be an integer of 3~8.

In one embodiment of the present disclosure, a multi-branched cationic phosphonium salt having a structure represented by Formula (III) is provided.

$$\{Z[P^+(R)_3]_n\}(X^-)_n \qquad (III)$$

In some embodiments of the present disclosure, R may be linear or branched $C_1$~$C_{10}$ alkyl group, X$^-$ may be an organic or inorganic anion, and Z may have a structure represented by Formula (IIb) or Formula (IIc):

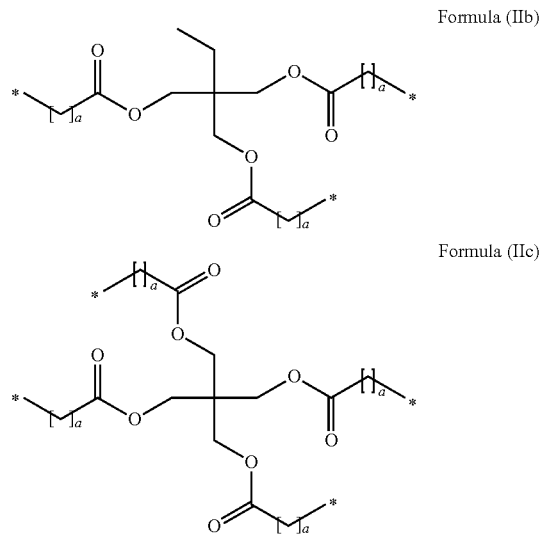

Formula (IIb)

Formula (IIc)

wherein a is an integer of 1~15. In Formulas (IIb) and (IIc), Z is connected to [P$^+$(R)$_3$] at the position marked by an asterisk (*), wherein n is an integer of 3~4.

In some embodiments of the present disclosure, X⁻ in Formula (III) may be an organic or inorganic anion with monovalent. For example, X⁻ may be $CH_3SO_3^-$, $I^-$, $CF_3COO^-$, $SCN^-$, $BF_4^-$, $CF_3SO_3^-$, $PF_6^-$, $FeCl_4^-$,

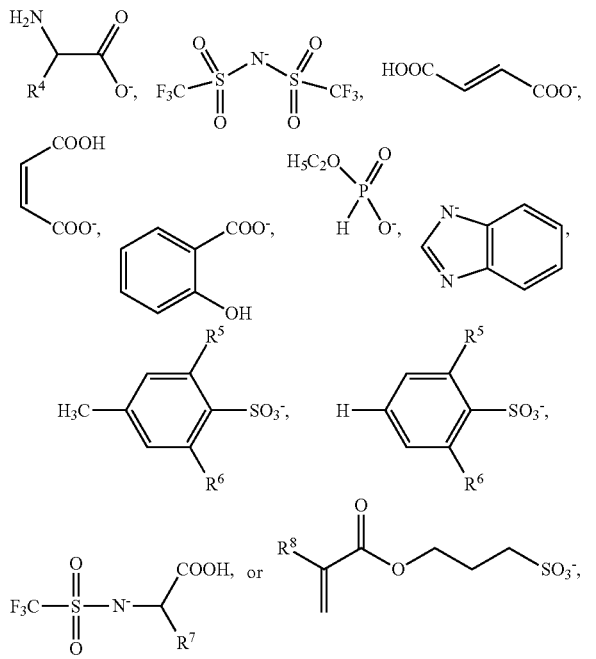

wherein $R^4$ may be $-CH_2COOH$ or $-(CH_2)_4-NH_2$; $R^5$ and $R^6$ may be H or $CH_3$; $R^7$ may be $-CH(CH_3)_2$, $-(CH_2)_2-CH(CH_3)_2$, $-CH(CH_3)-CH_2-CH_3$, or $-CH_2-C_6H_5$; $R^8$ may be $CH_3$ or H.

In the embodiments of the present disclosure, the multi-branched cationic phosphonium salt may be

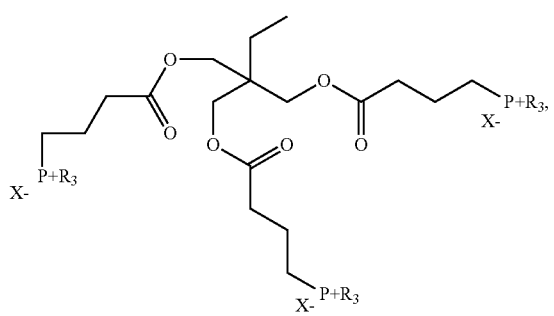

wherein R may be $C_1$~$C_5$ alkyl group, X⁻ may be $CH_3SO_3^-$, $CF_3COO^-$, $CF_3SO_3^-$

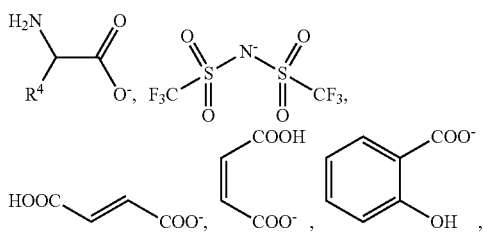

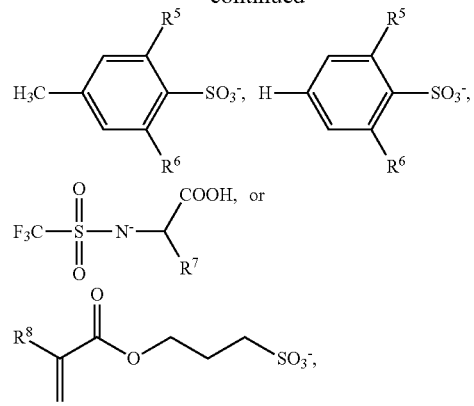

wherein $R^4$ may be $CH_2COOH$ or $-(CH_2)_4-NH_2$, $R^5$ and $R^6$ may be H or $CH_3$, $R^7$ is $-CH(CH_3)_2$, $-(CH_2)_2-CH(CH_3)_2$, $-CH(CH_3)-CH_2-CH_3$, or $-CH_2-C_6H_5$, and $R^8$ may be $CH_3$ or H.

In one embodiment of the present disclosure, the multi-branched cationic phosphonium salt may be trimethylolpropane tris[(tri-n-butylphosphonium)butyrate] tri(p-toluenesulfonate (P3-TOS). The chemical formula is as follows:

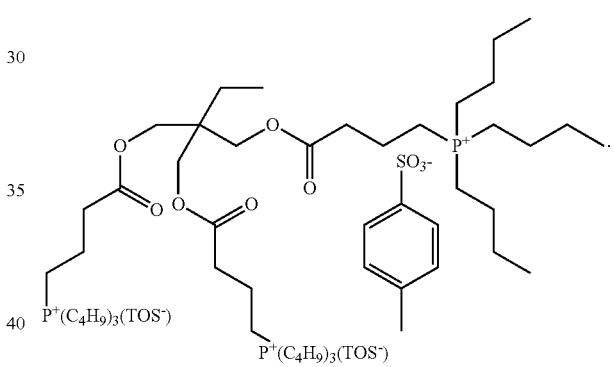

In some embodiments of the present disclosure, the multi-branched cationic phosphonium salt is a temperature sensitive material with a lower critical solution temperature (LCST). The phase change temperature (Tc) of the multi-branched cationic phosphonium salt may be 5~60° C. Because of the modified cation portion, the lower critical solution temperature (LCST) of the multi-branched cationic phosphonium salt synthesized in the present disclosure is near room temperature. Therefore, in the present disclosure, the multi-branched cationic phosphonium salt and water in the extract may be separated by using liquid-liquid phase separation or solid-liquid phase separation at a lower temperature, which is a low energy consumption process. Also, since the multi-branched cationic phosphonium salt is a temperature sensitive material, it may be easily recycled and reused by the change of temperature. In other word, as long as the temperature is higher than the LCST of the resulting multi-branched cationic phosphonium salt of the present disclosure, the multi-branched cationic phosphonium salt becomes insoluble in water, reducing the multi-branched cationic phosphonium salt remained in the aqueous layer. Therefore, after phase separation, a more pure water may be obtained and the multi-branched cationic phosphonium salt may be efficiently recycled. In addition, since there is no need to perform a heating process to a high temperature to recycle the multi-branched cationic phosphonium salt in the present disclosure, the energy consumption is reduced.

Another embodiment of the present disclosure provides a forward osmosis extract, including aforementioned multi-branched cationic phosphonium salt and water. The osmotic pressure of the forward osmosis extract monotonically increases with the increase of the mass molar concentration of the forward osmosis extract. However, the osmotic pressure and the mass molar concentration of the forward osmosis extract are not in a linear relationship.

In some embodiments of the present disclosure, the multi-branched cationic phosphonium salt included in the forward osmosis extract has a structure represented by Formula (I):

$$\{Z[P^+(R^1)(R^2)(R^3)]_n\}(X^-)_n \quad (I)$$

wherein each of $R^1$, $R^2$, and $R^3$ is independently linear or branched $C_1$~$C_{10}$ alkyl group, $X^-$ is an organic or inorganic anion, Z has a structure represented by Formula (IIa), Formula (IIb), Formula (IIc) or Formula (IId):

Formula (IIa)

Formula (IIb)

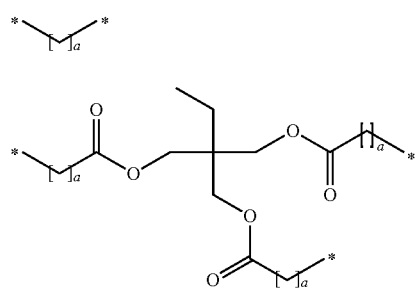

Formula (IIc)

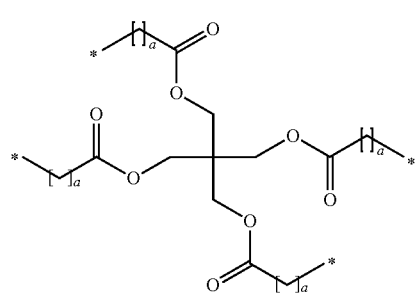

Formula (IId)

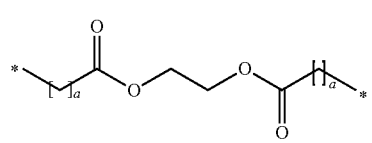

wherein a is an integer of 1~15, in Formulas (IIa)~(IId), Z is connected to $[P^+(R^1)(R^2)(R^3)]$ at the position marked by an asterisk (*), wherein n is an integer of 2~4. $X^-$ may be as defined in the aforementioned Formula (I).

In some embodiments of the present disclosure, the multi-branched cationic phosphonium salt included in the forward osmosis extract may be:

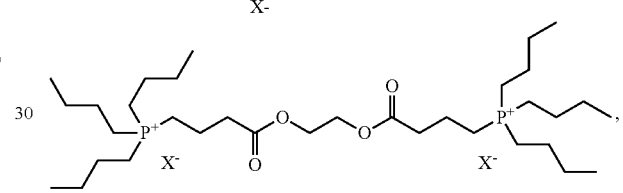

wherein $X^-$ may be as defined in the aforementioned Formula (I).

In one embodiment of the present disclosure, the multi-branched cationic phosphonium salt included in the forward osmosis extract may be 1,8-octanediyl-bis(tri-n-butylphosphonium) di(p-toluenesulfonate)(P2-TOS). The chemical formula is as follows:

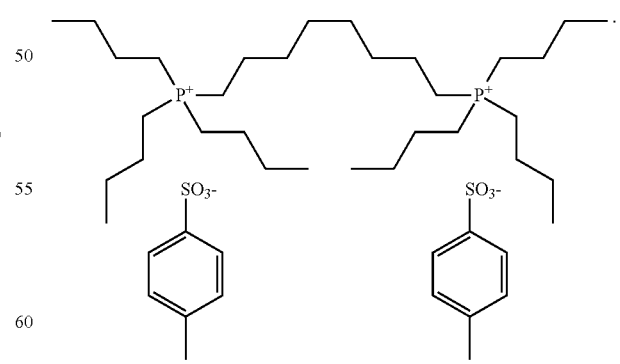

In one embodiment of the present disclosure, the multi-branched cationic phosphonium salt included in the forward osmosis extract may be 1,8-octanediyl-bis(tri-n-butylphosphonium) di(2,4,6-trimethyl-benzenesulfonate)(P2-TMBS).

The chemical formula is as follows:

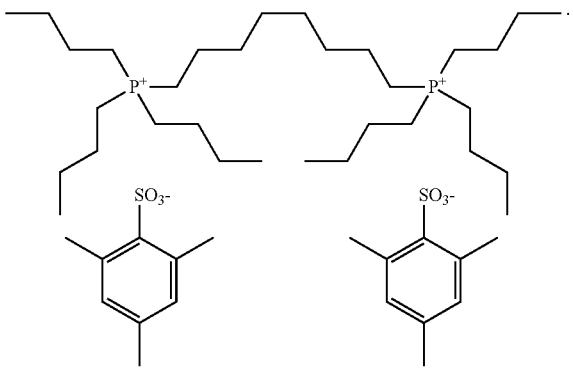

In one embodiment of the present disclosure, the multi-branched cationic phosphonium salt included in the forward osmosis extract may be trimethylolpropane tris[(tri-n-butylphosphonium)butyrate] tri(p-toluenesulfonate (P3-TOS). The chemical formula is as follows:

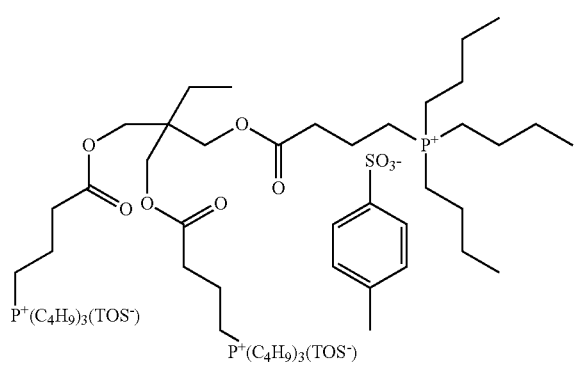

In one embodiment of the present disclosure, the multi-branched cationic phosphonium salt included in the forward osmosis extract may be 1,2-ethanediol bis[(tri-n-butylphosphonium)butyrate](P2a-TOS). The chemical formula is as follows:

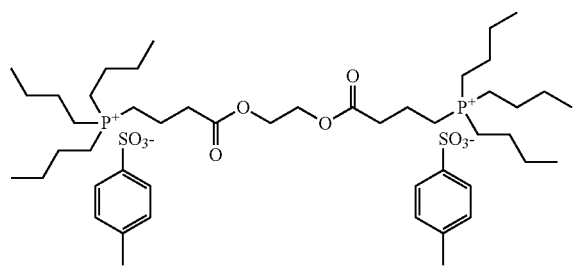

In one embodiment of the present disclosure, the multi-branched cationic phosphonium salt included in the forward osmosis extract may be 1,8-octanediyl-bis(tri-n-butylphosphonium) di(salicylic acid)(P2-SA). The chemical formula is as follows:

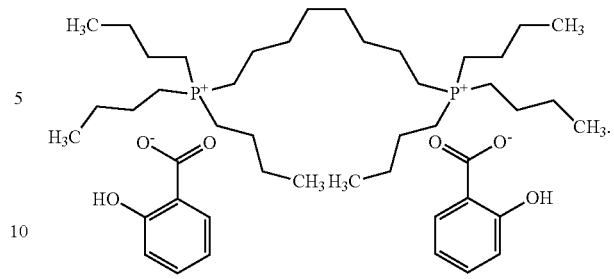

In one embodiment of the present disclosure, the multi-branched cationic phosphonium salt included in the forward osmosis extract may be 1,8-octanediyl-bis(tri-n-butylphosphonium) di(trifluoroacetic acid)(P2-TFA). The chemical formula is as follows:

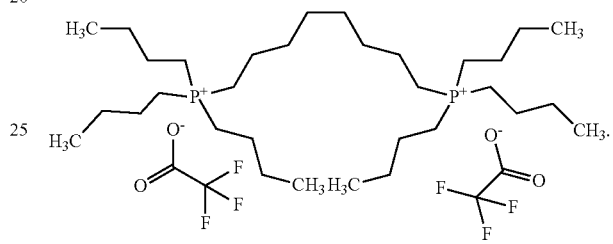

In some embodiments of the present disclosure, the concentration of the aforementioned forward osmosis extract is greater than or equal to 5 wt %. In some embodiments of the present disclosure, the forward osmosis extract may be applied to a forward osmosis seawater desalination technology. At this time, the concentration of the forward osmosis extract may be greater than, for example, 30 wt %, 50 wt %, or 60 wt %. It should be noted that the concentration of the forward osmosis extract is not limited to a specific range. As long as the osmotic pressure of the forward osmosis extract under the concentration is greater than the osmotic pressure of the raw material liquid (for example, seawater, protein, industrial wastewater, agriculture or livelihood wastewater), the effect of the forward osmosis extract may be normally expressed. Generally, the greater the difference between the osmotic pressure of the forward osmosis extract and the osmotic pressure of the raw material liquid, the better the extraction effect is. Therefore, a better extraction effect may be obtained when using an aqueous solution with a high concentration as the extract. However, in terms of cost, as long as the osmotic pressure of the forward osmosis extract under the concentration is greater than the osmotic pressure of the raw material liquid, it can be used in the present disclosure. Take the multi-branched cationic phosphonium salt P2-TOS provided by an embodiment of the present disclosure as an example; P2-TOS itself is a liquid solution, so it may be directly used as an extract under a concentration of 100 wt %. However, according to the value of osmotic pressure, the desired concentration of the P2-TOS aqueous solution may be arbitrarily formulated.

Another embodiment of the disclosure provides a forward osmosis seawater desalination process, including: providing the aforementioned forward osmosis extract and pure water on two sides of a semi-permeable membrane, respectively; and desalinating seawater by using a forward osmosis (FO) model.

Although the multi-branched cationic phosphonium salt provided by the present disclosure has a greater molecular weight since the cation portion has been modified, the viscosity is low. Therefore, it can be formulated into a high-concentration solution to make the formulated extract have a high osmotic pressure. Also, since the multi-branched cationic phosphonium salt provided by the present disclosure has a lower phase change temperature, it can be easily recycled during the application and has low energy consumption. In addition, when using the multi-branched cationic phosphonium salt provided by the present disclosure as an extract, the water flux can be effectively increased and the water production rate can be improved.

Below, preparation examples, comparative examples, and examples will be described in detail to explain the characteristics of the multi-branched cationic phosphonium salt provided by the present disclosure and the extract formulated therefrom.

Preparation Example 1

1,8-octanediyl-bis(tri-n-butylphosphonium)dibromide (P2-TOS)

At first, 1,8-octanediyl-bis(tri-n-butylphosphonium)dibromide (hereinafter called P2-Br for short) was synthesized:

(1) 80 g (0.4 mol) of tributylphosphine and 48.9 g (0.18 mol) of 1,8-dibromooctane were put into a 500 mL round bottom bottle. Then, 150 mL of anhydrous acetone was added and stirred at 40° C. for 48 hours.

(2) After the reaction finished, the reaction solution was slowly dripped into 1.5 L of ether. The white solid powder was obtained after filtration, and then it was washed several times with ether.

(3) The washed white solid was dried and 117 g of product P2-Br was obtained.

Next, 1,8-octanediyl-bis(tri-n-butylphosphonium) di(p-toluenesulfonate) (hereinafter called P2-TOS for short) was synthesized:

(1) 2.67 g (3.7 mmol) of P2-Br and 1.57 g (8.1 mmol) of sodium p-toluenesulfonate (TOS-Na) were dissolved in 13 g of deionized water and stirred at room temperature for 24 hours.

(2) After the reaction finished, the reaction mixture was extracted with 10 mL of ethyl acetate two times. The upper ethyl acetate layer was collected, and washed with 20 mL of deionized water three times for purification.

(3) The washed organic layer was vacuum concentrated at 30° C., and 1.6 g of the product P2-TOS was obtained.

The product P2-TOS was determined by NMR (1H-NMR, 400 MHz in $D_2O$): 0.81 (t, 18H, C$\underline{H}_3$CH$_2$—), 1.09 (m, 4H, —CH$_2$—), 1.1~1.5 (m, 32H, —CH$_2$—), 1.9~2.1 (t, 16H, PCH$_2$—), 2.25 (s, 6H, Ar—CH$_3$), 7.21 (d, 4H, ArH), 7.58 (d, 4H, ArH). The product P2-TOS has a chemical formula as follows:

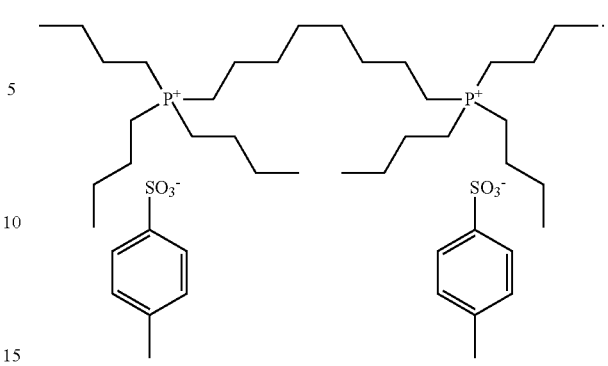

Preparation Example 2

1,8-octanediyl-bis(tri-n-butylphosphonium) di(2,4,6-trimethyl-benzenesulfonate) (P2-TMBS)

1,8-octanediyl-bis(tri-n-butylphosphonium) di(2,4,6-trimethyl-benzenesulfonate) (hereinafter called P2-TMBS for short) was synthesized:

(1) 10 g (14.7 mmol) of P2-Br and 6.8 g (29.6 mmol) of sodium 2,4,6-trimethyl-benzensulfonate (TMBS-Na) were dissolved in 40 g of deionized water and stirred at room temperature for 24 hours.

(2) After the reaction finished, 20 mL of ethyl acetate was added for extraction.

(3) The organic layer was collected and vacuum concentrated at 30° C., and 12.4 g of the product P2-TMBS was obtained.

The product P2-TMBS was determined by NMR ($^1$H-NMR, 400 MHz in $D_2O$): 0.8 (t, 18H, C$\underline{H}_3$CH$_2$—), 1.09 (m, 4H, —CH$_2$—), 1.1~1.5 (m, 32H, —CH$_2$—), 1.9~2.0 (t, 16H, PCH$_2$—), 2.12 (s, 6H, Ar—CH$_3$), 2.25 (s, 12H, Ar—CH$_3$), 6.88 (s, 4H, ArH). The product P2-TMBS has a chemical formula as follows:

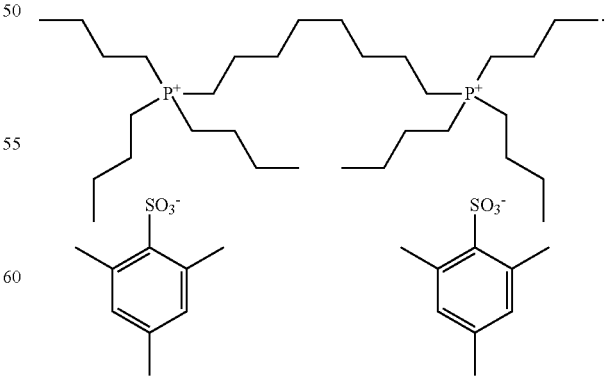

Preparation Example 3

Trimethylolpropane tris[(tri-n-butylphosphonium) butyrate] tri(p-toluenesulfonate) (P3-TOS)

At first, trimethylolpropane tris(4-bromobutyrate) was synthesized:
(1) 1 g (8.3 mmol) of trimethylolpropane was put in a 50 mL round bottom bottle and dissolved in 20 mL of anhydrous tetrahydrofuran (THF). Then, 1.1 g of NaH (60%) was slowly added and stirred by a stir bar at room temperature for 2 hours. Then, 5 g (27 mmol) of 4-bromobutyryl chloride was dripped into the solution at room temperature for overnight reaction.
(2) After the reaction finished, the reaction mixture was concentrated, and then 20 mL of ether was added. The mixture was filtrated to remove the solid. The obtained filtrate was washed with 50 mL of water three times and then was rotary-evaporated to dryness. 3.4 g of the product trimethylolpropane tris(4-bromobutyrate) was obtained.

Next, trimethylolpropane tris[(tri-n-butylphosphonium) butyrate] tribromide (hereinafter called P3-Br for short) was synthesized:
(1) 1.14 g (5.6 mmol) of tributylphosphine and 1.06 g (1.8 mmol) of trimethylolpropane tris(4-bromobutyrate) were put into a 50 mL round bottom bottle. Then, 10 mL of anhydrous acetone was added and stirred at 40° C. for 24 hours.
(2) After the reaction finished, the reaction solution was concentrated. 20 mL of water was added, and 50 mL of ether was added for wash three times. After the reaction solution was concentrated, 1.9 g of the product P3-Br was obtained.

Next, trimethylolpropane tris[(tri-n-butylphosphonium) butyrate] tri(p-toluenesulfonate (hereinafter called P3-TOS for short) was synthesized:
(1) 3 g (2.5 mmol) of P3-Br and 1.5 g (7.7 mmol) of sodium p-toluenesulfonate (TOS-Na) were dissolved in 55 g of deionized water and stirred at room temperature for 24 hours.
(2) After the reaction was finished, the reaction solution was extracted with 15 mL of ethyl acetate once.
(3) The organic layer was collected and vacuum concentrated at 30° C., and 2.5 g of the product P3-TOS was obtained.

The product P3-TOS was determined by NMR ($^1$H-NMR, 400 MHz in $D_2O$): 0.81 (t, 30H, C$\underline{H}_3$CH$_2$—), 1.2~1.5 (m, 38H, —CH$_2$—), 1.6~1.8 (br.s, 6H, —CH$_2$—), 1.95~2.1 (m, 24H, PCH$_2$—), 2.26 (s, 9H, Ar—CH$_3$), 2.42 (m, 6H, —CH$_2$CO—), 4.0 (s, 6H, —OCH$_2$—), 7.21 (d, 6H, ArH), 7.58 (d, 6H, ArH). The product P3-TOS has a chemical formula as follows:

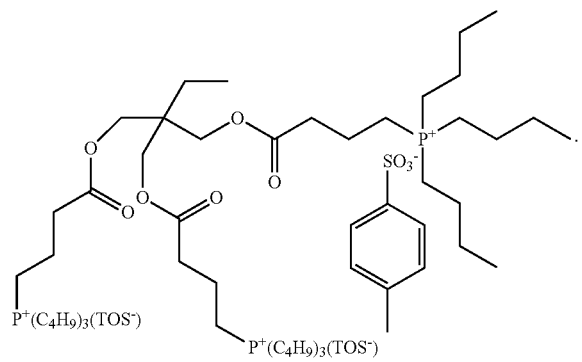

Preparation Example 4

1,2-ethanediol bis[(tri-n-butylphosphonium)butyrate] di(p-toluenesulfonate)) (P2a-TOS)

At first, 1,2-ethanediol bis(4-bromobutyrate) was synthesized:

(1) 0.795 g (12.8 mmol) of 1,2-ethanediol was put into a 50 mL round bottom bottle and dissolved in 20 mL of anhydrous tetrahydrofuran (THF). Then, 1.23 g of NaH (60%) was slowly added and stirred at room temperature for 2 hours. Then, 5.35 g (2.74 mmol) of 4-bromobutyryl chloride was dripped into the solution at room temperature for overnight reaction.

(2) After the reaction finished, the resulting mixture was concentrated, and then 20 mL of ether was added. The solution was filtrated to remove the solid. The obtained filtrate was washed with 50 mL of water three times. The washed filtrate was concentrated and 3 g of the product trimethylolpropane tris(4-bromobutyrate) was obtained.

Next, 1,2-ethanediol bis[(tri-n-butylphosphonium)butyrate] dibromide (hereinafter called P2a-Br for short) was synthesized:

(1) 3.2 g (15.8 mmol) of tributylphosphine and 2.85 g (7.9 mmol) of 1,2-ethanediol bis(4-bromobutyrate) were put into a 50 mL round bottom bottle. Then, 10 mL of anhydrous acetone was added and stirred at 40° C. for 24 hours.

(2) After the reaction finished, the reaction solution was concentrated, and then 60 mL of water was added. 150 mL of ether was added for wash three times. After the solution was concentrated, 5 g of the product P2a-Br was obtained.

Next, 1,2-ethanediol bis[(tri-n-butylphosphonium)butyrate] di(p-toluenesulfonate) (hereinafter called P2a-TOS for short) was synthesized:

(1) 5 g (6.5 mmol) of P2a-Br and 2.79 g (14.3 mmol) of sodium p-toluenesulfonate (TOS-Na) were dissolved in 20 g of deionized water and stirred at room temperature for 24 hours.

(2) After the reaction was finished, the reaction mixture was extracted with 25 mL of ethyl acetate once.

(3) The organic layer was collected and vacuum concentrated at 30° C., and 3 g of the product P2a-TOS was obtained.

The product P2a-TOS was determined by NMR (1H-NMR, 400 MHz in $D_2O$): 0.81 (t, 18H, CH$_3$CH$^2$—), 1.2~1.5 (m, 24H, —CH$^2$—), 1.6~1.8 (br.s, 4H, —CH$_2$—), 1.95~2.1 (m, 16H, PCH$_2$—), 2.26 (s, 6H, Ar—CH$_3$), 2.42 (m, 4H, —CH$_2$CO—), 4.2 (s, 4H, —OCH$_2$—), 7.21 (d, 4H, ArH), 7.58 (d, 4H, ArH). The product P2a-TOS has a chemical formula as follows:

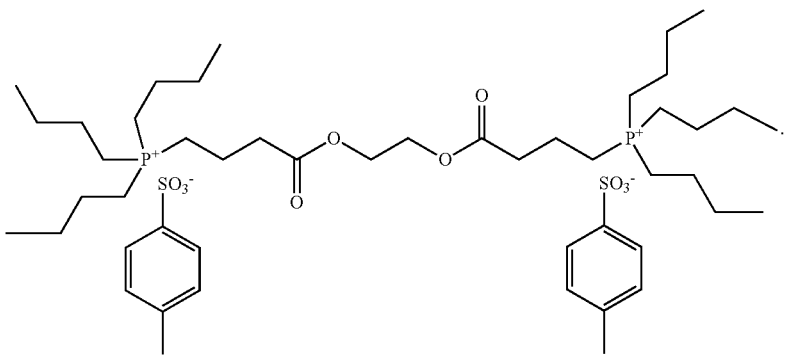

Preparation Example 5

1,8-octanediyl-bis(tri-n-butylphosphonium) di(salicylic acid)(P2-SA)

At first, P2-Br was synthesized according to the method described in Preparation Example 1. Next, 1,8-octanediyl-bis(tri-n-butylphosphonium) di(salicylic acid) (hereinafter called P2-SA for short) was synthesized according to the following steps:

(1) P2-Br was first converted to P2-OH (1,8-octanediyl-bis(tri-n-butylphosphonium)dihydroxide) by using an ion exchange resin. 20 g (36.4 mmol) of P2-OH and 10.1 g (72.8 mmol) of salicylic acid (SA) were dissolved in 120 g of deionized water with 3 g of ethanol. The mixture was stirred at room temperature for 24 hours.
(2) After the reaction finished, 80 mL of ethyl acetate was added for extraction.
(3) The organic layer was concentrated and about 16 g of the product P2-SA was obtained.

The product P2-SA was determined by NMR ($^1$H-NMR, 400 MHz in $D_2O$; ppm): 0.8 (t, 18H, $CH_3$—), 1.20 (m, 4H, —$CH_2$—), 1.25~1.45 (m, 32H, —$CH_2$—), 1.90~2.05 (m, 16H, $PCH_2$—), 6.81~6.86 (m, 4H, ArH), 7.32 (td, 2H, ArH), 7.70 (dd, 2H, ArH). The product P2-SA has a chemical formula as follows:

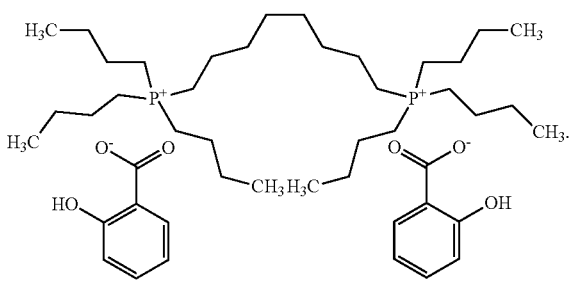 [SMILES: CCCC[P+](CCCC)(CCCC)CCCCCCCC[P+](CCCC)(CCCC)CCCC ; O=C([O-])c1ccccc1O ; O=C([O-])c1ccccc1O]

Preparation Example 6

1,8-octanediyl-bis(tri-n-butylphosphonium) di(trifluoroacetic acid)(P2-TFA)

At first, P2-Br was synthesized according to the method described in Preparation Example 1. Next, 1,8-octanediyl-bis(tri-n-butylphosphonium) di(trifluoroacetic acid)(hereinafter called P2-TFA for short) was synthesized according to the following steps:

(1) P2-Br was first converted to P2-OH (1,8-octanediyl-bis(tri-n-butylphosphonium)dihydroxide) by using an ion exchange resin. 20 g (36.4 mmol) of P2-OH and 8.3 g (72.8 mmol) of trifluoroacetic acid (TFA) were dissolved in 30 g of deionized water. The mixture was stirred at room temperature for 24 hours.
(2) After the reaction finished, 20 mL of ethyl acetate was added for extraction.
(3) The organic layer was concentrated and about 12 g of the product P2-TFA was obtained.

The product P2-TFA was determined by NMR ($^1$H-NMR, 400 MHz in $D_2O$; ppm): 0.81 (t, 18H, $CH_3$—), 1.23 (m, 4H, —$CH_2$—), 1.3~1.5 (m, 32H, —$CH_2$—), 2.0~2.2 (t, 16H, $PCH_2$—); ($^{19}$F-NMR, 400 MHz in $D_2O$; ppm): 75.54. The product P2-TFA has a chemical formula as follows:

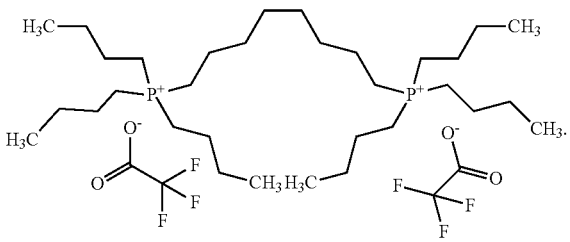 [SMILES: CCCC[P+](CCCC)(CCCC)CCCCCCCC[P+](CCCC)(CCCC)CCCC ; O=C([O-])C(F)(F)F ; O=C([O-])C(F)(F)F]

Comparative Example 1

Commercial tetrabutylphosphonium p-toluenesulfonate) (Aldrich 95 wt %) [$P_{4444}$][TOS] was used as the Comparative Example.

Comparative Example 2

The P2-Br synthesized in Comparative Example 1 was determined by NMR ($^1$H-NMR, 400 MHz in $D_2O$; ppm): 0.81 (t, 18H, $CH_3$—), 1.09 (m, 4H, —$CH_2$—), 1.1~1.5 (m, 32H, —$CH_2$—), 1.9~2.1 (t, 16H, $PCH_2$—). P2-Br has a chemical formula as follows:

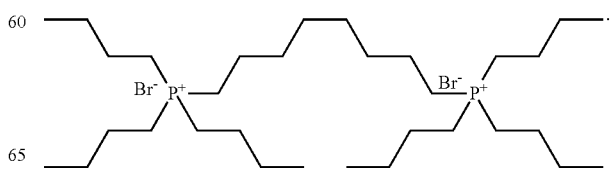

Comparative Example 3

1,2-ethanediol bis[(tri-n-butylphosphonium) acetyrate] dibromide)(hereinafter called P2a1-Br for short) was synthesized according to the following steps:

(1) 1 g (4.93 mmol) of tributylphosphine and 0.752 g (2.47 mmol) of 1,2-ethanediol bis(bromoacetyrate) were put into a 100 mL round bottom bottle. Then, 10 mL of anhydrous acetone was added and stirred at 40° C. for 48 hours.

(2) After the reaction finished, the reaction solution was concentrated. 40 mL of water was added, and 100 mL of ether was added for wash three times. After the reaction solution was concentrated, 1 g of the product P2a1-Br was obtained.

The product P2a1-Br was determined by NMR ($^1$H-NMR, 400 MHz in $D_2O$; ppm): 0.8 (t, 18H, $CH_3$—), 1.2~1.6 (m, 24H, —$CH_2$—), 2.3~2.3 (m, 12H, $PCH_2$—), 3.52 (d, 4H, —$CH_2$(CO)—), 4.4 (s, 4H, —$OCH_2$—). The product P2a1-Br has a chemical formula as follows:

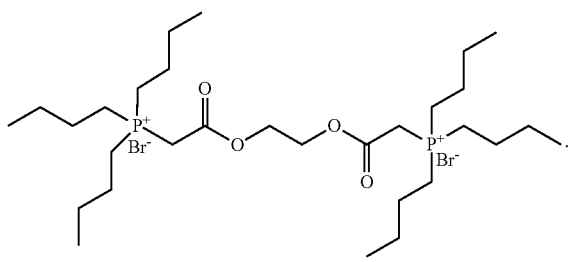 [SMILES: CCCC[P+](CCCC)(CCCC)CC(=O)OCCOC(=O)C[P+](CCCC)(CCCC)CCCC ; [Br-] ; [Br-]]

Comparative Example 4

Trimethylolpropane tris[(tri-n-butylphosphonium)butyrate] tribromide (hereinafter called P3-Br for short) was synthesized according to the following steps:

(1) 1.14 g (5.6 mmol) of tributylphosphine and 1.06 g (1.8 mmol) of trimethylolpropane tris(4-bromobutyrate) were put into a 50 mL round bottom bottle. Then, 10 mL of anhydrous acetone was added and stirred at 40° C. for 24 hours.

(2) After the reaction finished, the reaction solution was concentrated. 20 mL of water was added, and 50 mL of ether was added for wash three times. After the reaction solution was concentrated, 1.9 g of the product P3-Br was obtained.

The product P3-Br was determined by NMR ($^1$H-NMR, 400 MHz in $D_2O$; ppm): 0.81 (t, 30H, $CH_3$—), 1.2~1.5 (m, 38H, —$CH_2$—), 1.6~1.8 (br.s, 6H, —$CH_2$—), 1.95~2.1 (m, 24H, $PCH_2$—), 2.42 (m, 6H, —$CH_2CO$—), 4.0 (s, 6H, —$OCH_2$—). The product P3-Br has a chemical formula as follows:

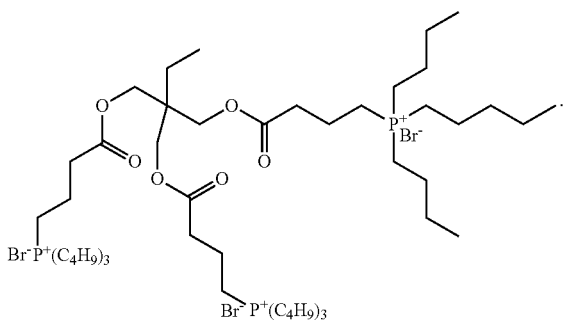

[Example 1] Measurement of Viscosity

The multi-branched cationic phosphonium salt P2-TOS obtained in Preparation Example 1, the multi-branched cationic phosphonium salt P2-TMBS obtained in Preparation Example 2, the multi-branched cationic phosphonium salt P3-TOS obtained in Preparation Example 3, and the multi-branched cationic phosphonium salt P2a-TOS obtained in Preparation Example 4 were respectively formulated into an aqueous solution with a concentration of 75 wt %. The viscosity was measured by viscosity meter Brookfield DV2TLVCJ0 at 20° C. The results are shown in Table 1.

TABLE 1

| 75 wt % 20° C. | viscosity (cp) |
| --- | --- |
| Preparation Example 1 | 94 |
| Preparation Example 2 | 110 |
| Preparation Example 3 | 40 |
| Preparation Example 4 | 61 |

To be operable, the viscosity of the material suitable for use as the extract is preferable 200 cp or less according to operating experience. If the viscosity is too high, the material is not suitable for use as an extract due to flow difficulty. Polymer materials are not suitable for use as an extract at a high concentration because operational difficulties caused by the problems with high viscosity. It can be seen in Table 1 that the multi-branched cationic phosphonium salts of Preparation Examples 1 to 4 of the present disclosure have a large molecular weight since they have been modified by cations. However, when they are formulated into a concentrate aqueous solution with 75 wt % of the multi-branched cationic phosphonium salt, the highest viscosity is only 110 cp, which is still within the operable viscosity range. In other words, the viscosity of the solution of the multi-branched cationic phosphonium salts of Preparation Examples 1 to 4 of the present disclosure do not significantly increase due to the increase of the molecular weight. Therefore, the multi-branched cationic phosphonium salts of Preparation Examples 1 to 4 of the present disclosure are not like the polymer material which cannot be used as an extract at a high concentration since the viscosity is too high.

[Example 2] Measurement of Osmotic Pressure

The multi-branched cationic phosphonium salt P2-TOS obtained in Preparation Example 1, the multi-branched cationic phosphonium salt P2-TMBS obtained in Preparation Example 2, the multi-branched cationic phosphonium salt P3-TOS obtained in Preparation Example 3, the multi-branched cationic phosphonium salt P2a-TOS obtained in Preparation Example 4, the multi-branched cationic phosphonium salt P2-SA obtained in Preparation Example 5, and the multi-branched cationic phosphonium salt P2-TFA obtained in Preparation Example 6 were respectively formulated into aqueous solutions at different concentrations. The osmotic pressure was measured by using a freezing point osmometer (OSMOMAT 030; GONOTEC) and a freezing point method.

It should be noted that when the concentration of the aqueous solution is greater than 30 wt %, the osmotic pressure is usually not measurable with instruments. However, the osmotic pressure of the aqueous solution with a concentration greater than 30 wt % can be predicted by using an extrapolation method according to the results of the osmotic pressure measurements of the aqueous solution with a low concentration. Thus, in the following examples of the present disclosure, the osmotic pressure of the aqueous solution prepared in Preparation Examples 1 to 4 at low concentrations were measured in advance and the simulation function of osmotic pressure related to the mass molar concentration was plotted. The simulation function was used to predict the osmotic pressure of the aqueous solution at high concentrations. Among them, the conversion formula between the mass molar concentration (molality) and weight percentage (wt %) was:

wt %=molality×Mw/[(molality×Mw)+1000]

Mw represents the molecular weight (g/mol) of the solute in the aqueous solution.

Table 2 shows the osmotic pressures of the multi-branched cationic phosphonium salt P2-TOS obtained in Preparation Example 1 being formulated into aqueous solutions at different concentrations. The actually obtained osmotic pressure and IL concentration data graph of P2-TOS measured by the freezing point method are shown in FIG. 1.

TABLE 2

| | | | | P2-TOS | | | | | |
|---|---|---|---|---|---|---|---|---|---|
| Mass molar concentration (mol/Kg) | 0.06 | 0.13 | 0.21 | 0.29 | 0.5 | 0.78 | 1.16 | 1.74 | 2.72 |
| Weight percent concentration (wt %) | 5 | 10 | 15 | 20 | 30 | 40 | 50 | 60 | 70 |
| Osmotic pressure (Osmol/Kg) | $0.152^a$ | $0.329^a$ | $0.493^a$ | $0.718^a$ | $1.188^b$ | $1.824^b$ | $2.703^b$ | $4.005^b$ | $6.148^b$ |

Note:
$^a$is the measured value and $^b$is the predicted value.

Figure 2:
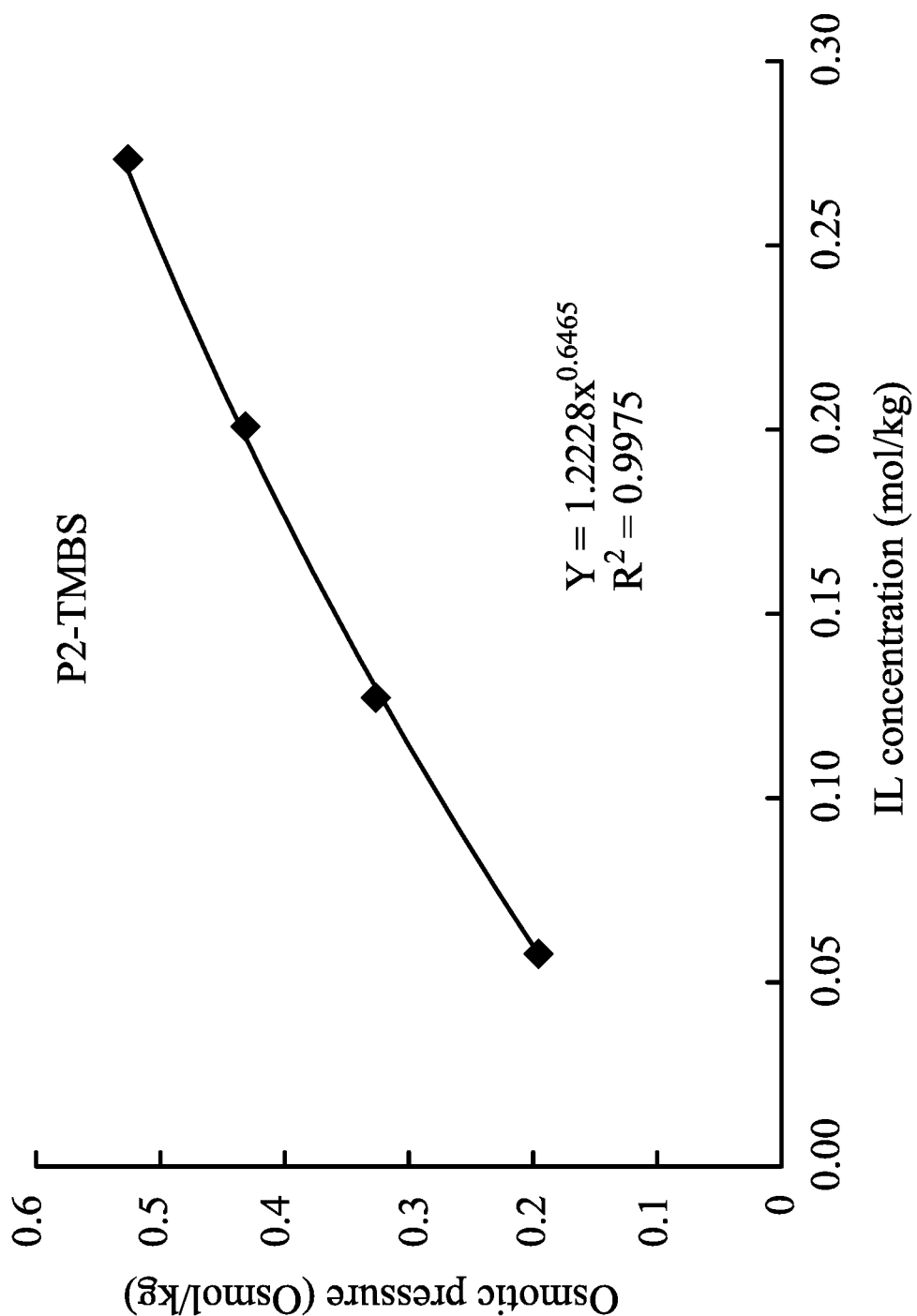
FIG. 2 illustrates the data graph of the actually obtained osmotic pressure and ionic liquid (IL) concentration of P2-TMBS.

Table 3 shows the osmotic pressures of the multi-branched cationic phosphonium salt P2-TMBS obtained in Preparation Example 2 being formulated into aqueous solutions at different concentrations. The actually obtained osmotic pressure and IL concentration data graph of P2-TMBS measured by the freezing point method are shown in FIG. 2.

TABLE 3

| | | | | P2-TMBS | | | | | |
|---|---|---|---|---|---|---|---|---|---|
| Mass molar concentration (mol/Kg) | 0.06 | 0.12 | 0.19 | 0.27 | 0.47 | 0.73 | 1.09 | 1.64 | 2.55 |
| Weight percent concentration (wt %) | 5 | 10 | 15 | 20 | 30 | 40 | 50 | 60 | 70 |
| Osmotic pressure (Osmol/Kg) | $0.19^a$ | $0.321^a$ | $0.426^a$ | $0.518^a$ | $0.749^b$ | $0.996^b$ | $1.295^b$ | $1.683^b$ | $2.239^b$ |

Note:
$^a$ is the measured value and $^b$ is the predicted value.

Figure 3:
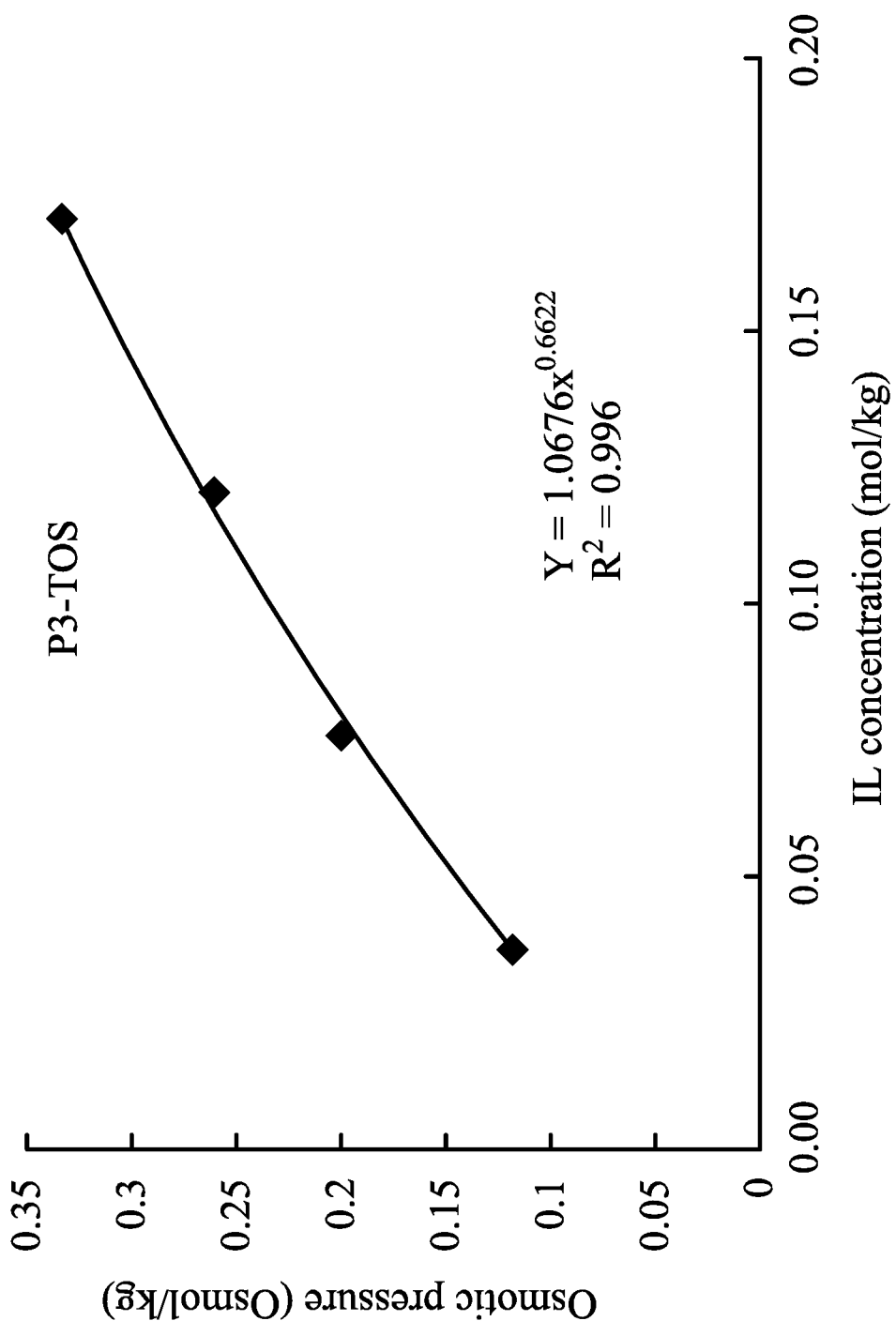
FIG. 3 illustrates the data graph of the actually obtained osmotic pressure and ionic liquid (IL) concentration of P3-TOS.

Table 4 shows the osmotic pressure of the multi-branched cationic phosphonium salt P3-TOS obtained in Preparation Example 3 being formulated into aqueous solutions at different concentrations. The actually obtained osmotic pressure and IL concentration data graph of P3-TOS measured by the freezing point method are shown in FIG. 3.

TABLE 4

| | P3-TOS | | | | | | | | |
|---|---|---|---|---|---|---|---|---|---|
| Mass molar concentration (mol/Kg) | 0.04 | 0.08 | 0.12 | 0.17 | 0.29 | 0.46 | 0.68 | 1.03 | 1.60 |
| Weight percent concentration (wt %) | 5 | 10 | 15 | 20 | 30 | 40 | 50 | 60 | 70 |
| Osmotic pressure (Osmol/Kg) | 0.116 [a] | 0.202 [a] | 0.259 [a] | 0.329 [a] | 0.474 [b] | 0.635 [b] | 0.830 [b] | 1.086 [b] | 1.455 [b] |

Note:
[a] is the measured value and [b] is the predicted value.

Figure 4:
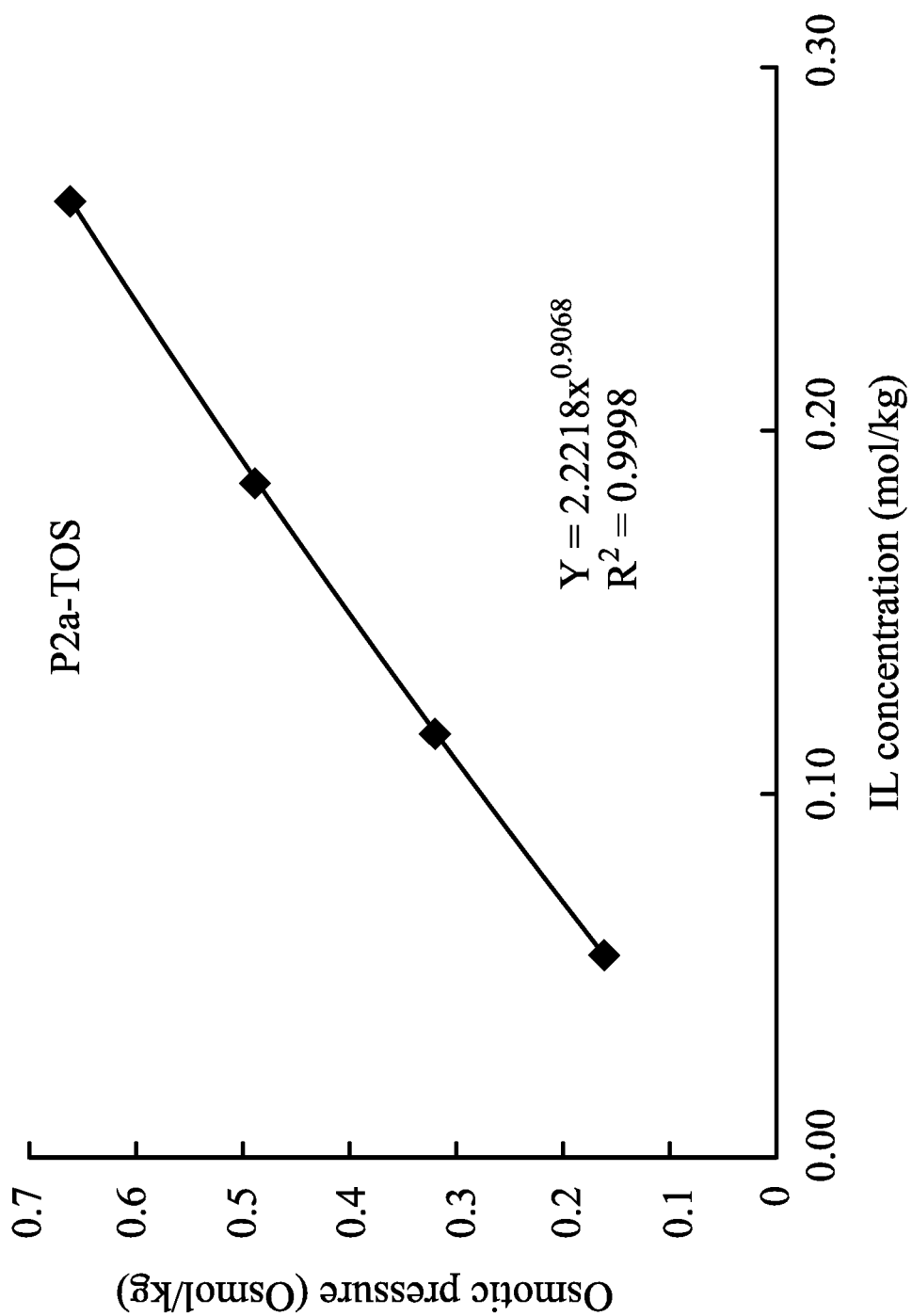
FIG. 4 illustrates the data graph of the actually obtained osmotic pressure and ionic liquid (IL) concentration of P2a-TOS.

Table 5 shows the osmotic pressure of the multi-branched cationic phosphonium salt P2a-TOS obtained in Preparation Example 4 being formulated into aqueous solutions at different concentrations. The actually obtained osmotic pressure and IL concentration data graph of P2a-TOS measured by the freezing point method are shown in FIG. 4.

TABLE 5

| | P2a-TOS | | | | | | | | |
|---|---|---|---|---|---|---|---|---|---|
| Mass molar concentration (mol/Kg) | 0.06 | 0.12 | 0.19 | 0.26 | 0.45 | 0.70 | 1.06 | 1.58 | 2.46 |
| Weight percent concentration (wt %) | 5 | 10 | 15 | 20 | 30 | 40 | 50 | 60 | 70 |
| Osmotic pressure (Osmol/Kg) | 0.161 [a] | 0.319 [a] | 0.49 [a] | 0.657 [a] | 1.082 [b] | 1.616 [b] | 2.334 [b] | 3.371 [b] | 5.032 [b] |

Note:
[a] is the measured value and [b] is the predicted value.

In order to confirm the correctness of the predicted value, the following tests were carried out. A U-shaped tube was installed with a forward osmosis (FO) film in the middle, 75 wt % of P2-TOS aqueous solution was put in one end and 11.2 wt % of NaCl aqueous solution was put in the other end (The osmotic pressure of NaCl aqueous solution at this concentration is about 3.2 times the osmotic pressure of seawater). After standing at a temperature of 22° C. for a period of time, the liquid level of the 75 wt % P2-TOS aqueous solution rose and the liquid level of the 11.2 wt % NaCl aqueous solution decreased. This means that the 75 wt % P2-TOS aqueous solution has a higher osmotic pressure than that of the 11.2 wt % NaCl aqueous solution (about 3.85 Osmol/kg). It can be seen in Table 2 that the osmotic pressure of the 70 wt % P2-TOS aqueous solution predicted by extrapolation is 6.148 (Osmol/Kg), which is higher than 3.85 Osmol/kg and is consistent with the above results. It shows that the osmotic pressure predicted by the extrapolation is informative.

Table 6 shows the osmotic pressure of the multi-branched cationic phosphonium salt P2-SA obtained in Preparation Example 5 being formulated into aqueous solutions at different concentrations.

TABLE 6

| | P2-SA | | | | |
|---|---|---|---|---|---|
| | Mass molar concentration (mol/Kg) | | | | |
| | 0.14 | 0.32 | 0.54 | 0.84 | 1.27 |
| Weight percent concentration (wt %) | 10 | 20 | 30 | 40 | 50 |
| Osmotic pressure (Osmol/Kg) | 0.085[a] | 0.190[a] | 0.998[a] | 1.113[a] | 1.37[a] |

Note:
a is the measured value.

Table 7 shows the osmotic pressure of the multi-branched cationic phosphonium salt P2-TFA obtained in Preparation Example 6 being formulated into aqueous solutions at different concentrations.

TABLE 7

| | P2-TFA | | | | |
|---|---|---|---|---|---|
| | Mass molar concentration (mol/Kg) | | | | |
| | 0.15 | 0.34 | 0.58 | 0.90 | 1.35 |
| Weight percent concentration (wt %) | 10 | 20 | 30 | 40 | 50 |
| Osmotic pressure (Osmol/Kg) | 0.418[a] | 0.866[a] | 1.154[a] | 1.715[a] | 3.090[a] |

Note:
a is the measured value.

According to the results of Tables 2~7, the osmotic pressure increases relative to the increase of the concentration of the multi-branched cationic phosphonium salt aqueous solution. Specifically, the osmotic pressure of the multi-branched cationic phosphonium salt aqueous solution is monotonically increasing with the mass molar concentration. However, the osmotic pressure and the mass molar concentration do not have a linear relationship. In particular, it can be seen from Table 2 that when the concentration of the aqueous solution prepared by Preparation Example 1 was between 30 and 40 wt %, the osmotic pressure can be greater than the osmotic pressure of seawater. Therefore, it is suitable for use in seawater desalination as a forward osmosis extract. Similarly, it can be seen in Tables 3~7 that when the concentration of the aqueous solution prepared by Preparation Example 2 was between 40 and 50 wt %, the concentration of the aqueous solution prepared by Preparation Example 3 was between 60 and 70 wt %, the concentration of the aqueous solution prepared by Preparation Example 4 was between 30 and 40 wt %, the concentration of the aqueous solution prepared by Preparation Example 5 was between 40 and 50 wt %, and the concentration of the aqueous solution prepared by Preparation Example 6 was between 30 and 40 wt %, the osmotic pressure can be greater than the osmotic pressure of seawater (1.2 Osmol/Kg). Therefore, it is suitable for use in seawater desalination as a forward osmosis extract.

In addition, according to the osmotic pressures of different raw material solutions, those skilled in the art may refer to the results shown in Tables 2~7 to select appropriate multi-branched cationic phosphonium salt species and an appropriate concentration for the extract formulated thereof, to be applied to a water extraction process with different raw material solutions.

[Example 3] Measurement of Phase Transition Temperature

The multi-branched cationic phosphonium salt P2-TOS obtained in Preparation Example 1, the multi-branched cationic phosphonium salt P2-TMBS obtained in Preparation Example 2, the multi-branched cationic phosphonium salt P3-TOS obtained in Preparation Example 3, the multi-branched cationic phosphonium salt P2a-TOS obtained in Preparation Example 4, the multi-branched cationic phosphonium salt P2-SA obtained in Preparation Example 5, the multi-branched cationic phosphonium salt P2-TFA obtained in Preparation Example 6, and the $[P_{444}][TOS]$ of the Comparative Example 1, P2-Br of the Comparative Example 2, P2a1-Br of the Comparative Example 3, P3-Br of the Comparative Example 4 were respectively formulated into aqueous solutions at different concentrations and slowly warmed up until the solutions started to fog. The minimum temperature at which the solution begins to fog (cloud point temperature; Tc) is the phase transition temperature. The results of measured Tc (° C.) are shown in Table 6.

TABLE 8

| | Concentration (wt %) | | | | | | | | |
|---|---|---|---|---|---|---|---|---|---|
| | 5 | 10 | 20 | 30 | 40 | 50 | 60 | 65 | 75 |
| Preparation Example 1 | — | 49 | 39 | 38 | 39 | 40 | 46 | 53 | — |
| Preparation Example 2 | 28 | 24 | 23 | 24 | 26 | 28 | 31 | — | — |
| Preparation Example 3 | 37 | 17 | 11 | 12 | 15 | 17 | 20 | 22 | 46 |
| Preparation Example 4 | — | 49 | 38 | 39 | 41 | 44 | 50 | — | — |
| Preparation Example 5 | — | — | 12 | 12 | — | 15 | 20 | — | — |
| Preparation Example 6 | — | — | 26 | 25 | — | 26 | 29 | — | — |
| Comparative Example 1 | — | — | 55 | 54 | 55 | 57 | — | — | — |
| Comparative Example 2 | No phase change | | | | | | | | |
| Comparative Example 3 | No phase change | | | | | | | | |
| Comparative Example 4 | No phase change | | | | | | | | |

In Table 8, the aqueous solution prepared by the product P2-TOS was represented by "Preparation Example 1", the aqueous solution prepared by the product P2-TMBS was represented by "Preparation Example 2", the aqueous solution prepared by the product P3-TOS was represented by "Preparation Example 3", the aqueous solution prepared by the product P2a-TOS was represented by "Preparation Example 4", the aqueous solution prepared by the product P2-SA was represented by "Preparation Example 5", the aqueous solution prepared by the product P2-TFA was represented by "Preparation Example 6", and the aqueous solution prepared by $[P_{4444}]$ [TOS] was represented by "Comparative Example 1", the aqueous solution prepared by P2-Br was represented by "Comparative Example 2", the aqueous solution prepared by P2a1-Br was represented by "Comparative Example 3", the aqueous solution prepared by P3-Br was represented by "Comparative Example 4". It can be seen from Table 8 that the phase transition temperature of the 40 wt % $[P_{4444}]$ [TOS] aqueous solution was about 55° C. If it was used as the extract, the energy consumption would be increased when recycling the extract because the phase transition temperature is too high.

By comparison, under the same concentration conditions (40 wt %), the phase transition temperatures of the aqueous solution of multi-branched cationic phosphonium salts prepared by Preparation Examples 1~4 were lower than the phase transition temperature of the $[P_{4444}]$ [TOS] aqueous solution. For example, the phase transition temperature of the 40 wt % aqueous solution of Preparation Example 1 was about 39° C., the phase transition temperature of the 40 wt % aqueous solution of Preparation Example 2 was about 26° C., the phase transition temperature of the 40 wt % aqueous solution of Preparation Example 4 was about 41° C., and the phase transition temperature of the 40 wt % aqueous solution of Preparation Example 3 further decreased to about 15° C. In addition, it can be realized from Table 8 that, under the same concentration conditions (such as 20~50 wt %), the phase transition temperatures of the aqueous solutions of multi-branched cationic phosphonium salts prepared by Preparation Examples 5 and 6 were lower than the phase transition temperature of the $[P_{4444}]$ [TOS] aqueous solution.

It was found that when the aqueous solutions of Preparation Examples 1~6 were used as the extract, the recycling of the extract was facilitated and energy consumption was decreased.

Comparing the characteristics of osmotic pressure and phase transition temperature of Examples 1 and 2, among the multi-branched cationic phosphonium salts prepared by the present disclosure, P2-TOS of Preparation Example 1 has a higher osmotic pressure and a phase transition temperature lower than that of [P$_{4444}$][TOS], which has the best effect. Below, the multi-branched cationic phosphonium salts of Preparation Examples 1~4 were formulated as extracts and the forward osmosis (FO) verification was conducted.

[Example 4] Forward Osmosis (FO) Verification

Dow filmtec tw30-3012-500 (semi-permeable membrane) was used. The area was 8×8 cm, and the cross flow was 25 cm/s. The feed solution was pure water. The extracts were 75 wt % P2-TOS aqueous solution, 75 wt % P2-TMBS aqueous solution, 50 wt % P2a-TOS aqueous solution, or 70 wt % [P$_{4444}$][TOS] aqueous solution. Forward osmosis verification was performed using FO model (active layer faced the feed solution, AL-FS). The results are shown in Table 9.

TABLE 9

| Raw material solution | extract | Semi-permeable membrane$^a$ | Operating mode | Water flux (LMH)$^b$ |
|---|---|---|---|---|
| Pure water | 75 wt % P2-TOS aqueous solution | membrane$^a$ | FO | 3.09 |
| Pure water | 75 wt % P2-TMBS aqueous solution | membrane$^a$ | FO | 3.04 |
| Pure water | 50 wt % P2a-TOS aqueous solution | membrane$^a$ | FO | 2.0 |
| Pure water | 70 wt % [P$_{4444}$][TOS] aqueous solution | membrane$^a$ | FO | 1.31 |

Note:
$^a$represents DOW FILMTEC ™ membrane;
$^b$represents the average flux of the beginning 60 minutes.

It can be seen from Table 9 that when the extract was the 70 wt % [P$_{4444}$][TOS] aqueous solution, the water flux was only 1.31 (LMH). In contrast, the water flux of the 75 wt % P2-TOS aqueous solution prepared by Preparation Example 1 of the present disclosure was 3.09 (LMH), and the water flux was increased about 2.3 times. The water flux of the 75 wt % P2-TMBS aqueous solution prepared by Preparation Example 2 was 3.04 (LMH), and the water flux was increased about 2.3 times. The water flux of the 50 wt % P2a-TOS aqueous solution prepared by Preparation Example 4 was 2.0 (LMH), and the water flux was increased about 1.5 times.

As evidenced by the results of the above Examples, although the cationic portion of the multi-branched cationic phosphonium salt has been modified so the molecular weight is increased, when formulated into extracts, it possesses characteristics of low viscosity, high osmotic pressure, and low phase transition temperature. Thus, when using the multi-branched cationic phosphonium salt provided by the present disclosure to formulate an extract, it has the advantage of being easily recycled and having low energy consumption. Furthermore, when using the multi-branched cationic phosphonium salt provided by the present disclosure to formulate an extract, the water flux can be effectively increased, thereby increasing the water production rate.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:
1. A multi-branched cationic phosphonium salt, having a structure of Formula (I):

{Z[P$^+$(R$^1$)(R$^2$)(R$^3$)]$_n$}(X$^-$)$_n$     (I)

wherein each of R$^1$, R$^2$, and R$^3$ is independently linear or branched C$_1$~C$_{10}$ alkyl group, wherein X$^-$ is an organic or inorganic anion, and Z has a structure represented by Formula (IIb) or Formula (IIc):

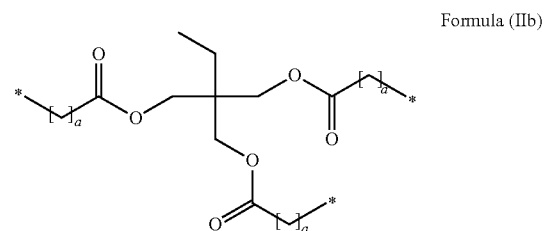

Formula (IIb)

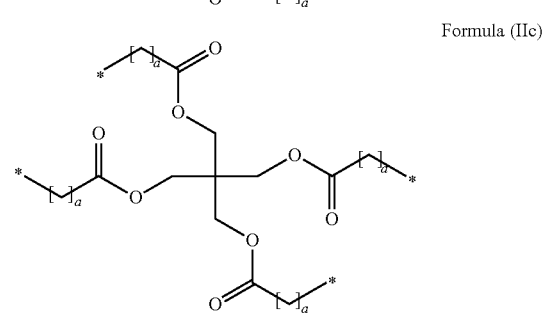

Formula (IIc)

wherein a is an integer of 1-15, in Formulas (IIb) and (IIc), Z is connected to [P$^+$(R$^1$)(R$^2$)(R$^3$)] at the position marked by an asterisk (*) wherein n is an integer of 3-4.

2. The multi-branched cationic phosphonium salt as claimed in claim 1,
wherein X$^-$ selected form the group consisting of is CH$_3$SO$_3^-$, I$^-$, CF$_3$COO$^-$, SCN$^-$, BF$_4^-$, CF$_3$SO$_3^-$, PF$_6^-$, FeCl$_4^-$,

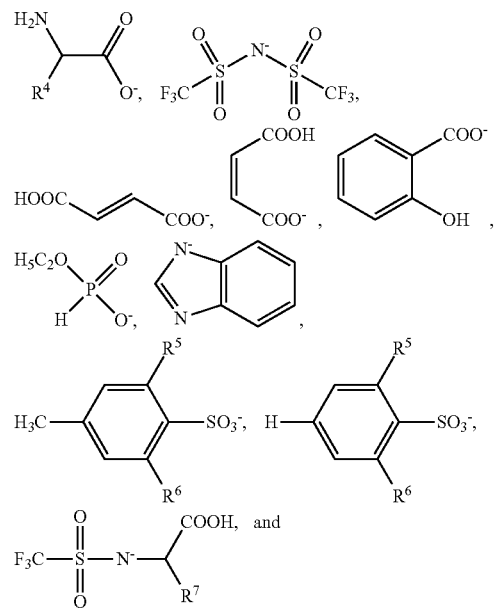

-continued

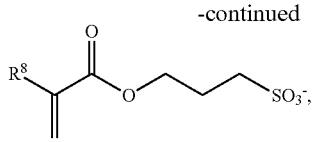

wherein $R^4$ is $CH_2COOH$ or $—(CH_2)_4—NH_2$, $R^5$ and $R^6$ are H or $CH_3$, $R^7$ is $—CH(CH_3)_2$, $—(CH_2)_2—CH(CH_3)_2$, $—CH(CH_3)—CH_2—CH_3$, or $—CH_2—C_6H_5$, and $R^8$ is $CH_3$ or H.

3. The multi-branched cationic phosphonium salt as claimed in claim 1, wherein each of $R^1$, $R^2$, and $R^3$ is independently $C_1$-$C_8$ alkyl groups.

4. The multi-branched cationic phosphonium salt as claimed in claim 1, wherein each of $R^1$, $R^2$, and $R^3$ is independently $C_1$-$C_5$ alkyl groups.

5. The multi-branched cationic phosphonium salt as claimed in claim 1, wherein a is an integer of 3-8.

6. A multi-branched cationic phosphonium salt, having a structure of Formula (III):

wherein R is linear or branched $C_1$~$C_{10}$ alkyl group, $X^-$ is an organic or inorganic anion, and Z has a structure of Formula (IIb) or Formula (IIc):

Formula (IIb)

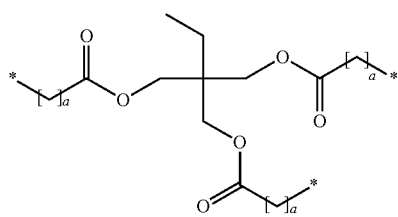

Formula (IIc)

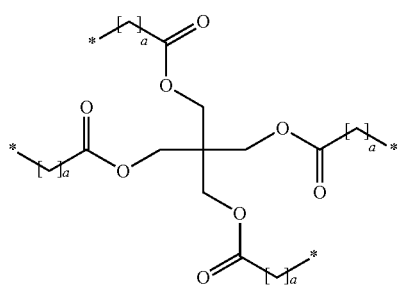

wherein a is an integer of 1-15, in Formulas (IIb) and (IIc), Z is connected to $[P^+(R)_3]$ at the position marked by an asterisk (*) wherein n is an integer of 3-4.

7. The multi-branched cationic phosphonium salt as claimed in claim 6, wherein $X^-$ selected form the group consisting of is $CH_3SO_3^-$, $CF_3COO^-$, $BF_4^-$, $CF_3SO_3^-$, $PF_6^-$, $FeCl_4^-$,

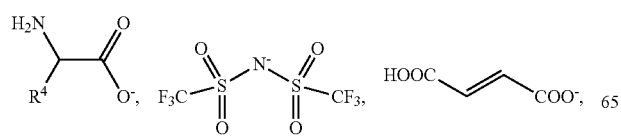

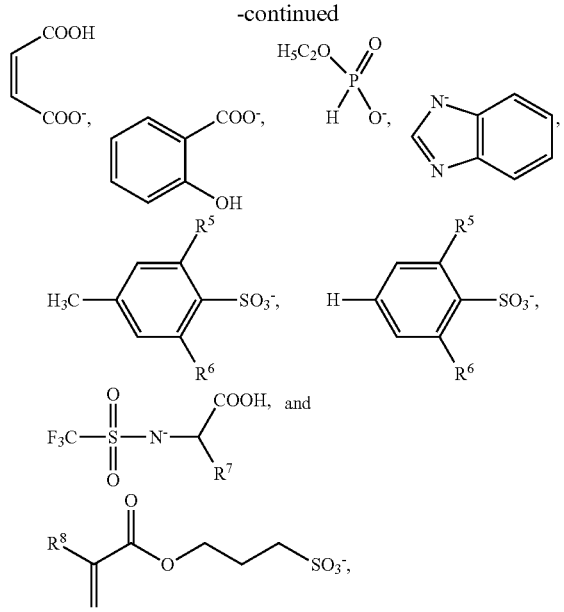

wherein $R^4$ is $CH_2COOH$ or $—(CH_2)_4—NH_2$, $R^5$ and $R^6$ are H or $CH_3$, $R^7$ is $—CH(CH_3)_2$, $—(CH_2)_2—CH(CH_3)_2$, $—CH(CH_3)—CH_2—CH_3$, or $—CH_2—C_6H_5$, and $R^8$ is $CH_3$ or H.

8. The multi-branched cationic phosphonium salt as claimed in claim 6, wherein the multi-branched cationic phosphonium salt

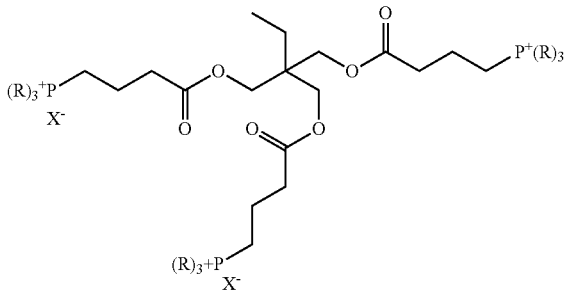

wherein R is $C_1$~$C_5$ alkyl group, $X^-$ selected form the group consisting of $CH_3SO_3^-$, $CF_3COO^-$, $CF_3SO_3^-$,

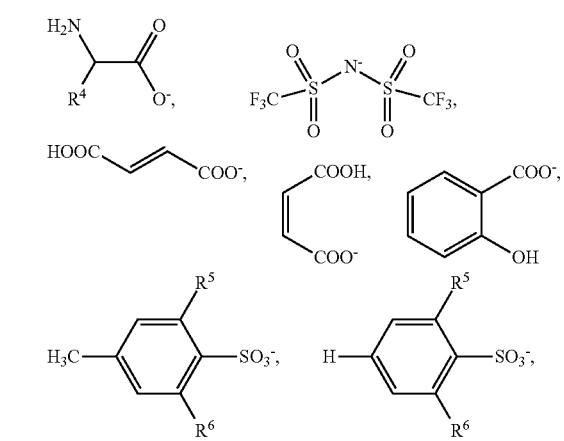

-continued

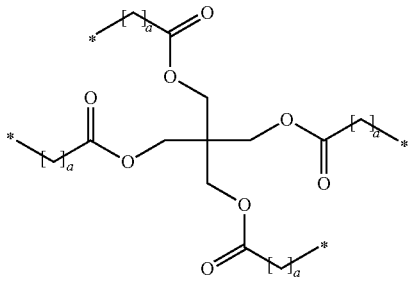

wherein R⁴ is CH₂COOH or —(CH₂)₄—NH₂, R⁵ and R⁶ are H or CH₃, R⁷ is —CH(CH₃)₂, —(CH₂)₂—CH(CH₃)₂, —CH(CH₃)—CH₂—CH₃, or —CH₂—C₆H₅, and R⁸ is CH₃ or H.

9. The multi-branched cationic phosphonium salt as claimed in claim 6, wherein a is an integer of 3-8.

10. The multi-branched cationic phosphonium salt as claimed in claim 6, wherein the multi-branched cationic phosphonium salt is trimethylolpropane tris[(tri-n-butylphosphonium)butyrate] tri(p-toluenesulfonate) (P3-TOS).

11. A forward osmosis extract, comprising:
a multi-branched cationic phosphonium salt, having a structure of Formula (I):

{Z[P⁺(R¹)(R²)(R³)]ₙ}(X⁻)ₙ     (I)

wherein each of R¹, R², and R³ is independently linear or branched C₁~C₁₀ alkyl group, wherein X⁻ is an organic or inorganic anion, Z has a structure of Formula (IIb) or Formula (IIc):

Formula (IIb)

Formula (IIc)

wherein a is an integer of 1-15, in Formulas (IIb) and (IIc), Z is connected to [P⁺(R¹)(R²)(R³)] at the position marked by an asterisk (*) wherein n is an integer of 2-4; and water, wherein a concentration of the forward osmosis extract is greater than or equal to 5 wt %.

12. The forward osmosis extract as claimed in claim 11, wherein the osmotic pressure of the forward osmosis extract monotonically increases with the increase of the mass molar concentration of the forward osmosis extract.

13. The forward osmosis extract as claimed in claim 11, wherein the multi-branched cationic phosphonium salt is 1,8-octanediyl-bis(tri-n-butylphosphonium) di(p-toluenesulfonate) (P2-TOS), 1,8-octanediyl-bis(tri-n-butylphosphonium) di(2,4,6-trimethyl-benzenesulfonate) (P2-TMBS), trimethylolpropane tris[(tri-n-butylphosphonium)butyrate] tri(p-toluenesulfonate) (P3-TOS), 1,2-Ethanediol bis[(tri-n-butylphosphonium)butyrate]) (P2a-TOS), 1,8-octanediyl-bis(tri-n-butylphosphonium) di(salicylic acid)(P2-SA), or 1,8-octanediyl-bis(tri-n-butylphosphonium) di(trifluoroacetic acid)(P2-TFA).

* * * * *